US012161422B2

(12) United States Patent
Wright et al.

(10) Patent No.: US 12,161,422 B2
(45) Date of Patent: Dec. 10, 2024

(54) MEDICAL DEVICE VISUALIZATION

(71) Applicant: Affera, Inc., Newton, MA (US)

(72) Inventors: Geoffrey Peter Wright, Winchester, MA (US); Doron Harlev, Brookline, MA (US)

(73) Assignee: AFFERA, INC., Watertown, MA (US)

( * ) Notice: Subject to any disclaimer, the term of this patent is extended or adjusted under 35 U.S.C. 154(b) by 0 days.

(21) Appl. No.: 18/183,868

(22) Filed: Mar. 14, 2023

(65) Prior Publication Data
US 2023/0320787 A1    Oct. 12, 2023

Related U.S. Application Data

(63) Continuation of application No. 17/820,549, filed on Aug. 17, 2022, now abandoned, which is a
(Continued)

(51) Int. Cl.
*A61B 34/10* (2016.01)
*A61B 34/00* (2016.01)
*G06T 15/30* (2011.01)

(52) U.S. Cl.
CPC .............. *A61B 34/10* (2016.02); *A61B 34/25* (2016.02); *G06T 15/30* (2013.01); *A61B 2034/102* (2016.02); *A61B 2034/105* (2016.02)

(58) Field of Classification Search
CPC ... A61B 34/10; A61B 34/25; A61B 2034/102; A61B 2034/105; A61B 34/20;
(Continued)

(56) References Cited

U.S. PATENT DOCUMENTS

| 4,734,690 A | 3/1988 | Waller |
| 5,276,785 A | 1/1994 | MacKinlay et al. |

(Continued)

FOREIGN PATENT DOCUMENTS

| WO | 2005063125 | 7/2005 |
| WO | 2017192746 | 11/2017 |
| WO | 2017192781 | 11/2017 |

OTHER PUBLICATIONS

Hilbert, Sebastian et al., "Real-Time Magnetic Resonance-guided ablation of typical right atrial flutter using a combination of active catheter tracking and passive catheter visualization in main: initial results from a consecutive patient series", Aug. 27, 2005, 6 pages.
(Continued)

*Primary Examiner* — Xilin Guo
(74) *Attorney, Agent, or Firm* — Tarolli, Sundheim, Covell & Tummino LLP

(57) ABSTRACT

Systems and methods present multiple images of a three-dimensional model, including a three-dimensional representation of an anatomic structure and a representation of a medical device relative to the anatomic structure, on a graphical user interface. The multiple images correspond to different views (e.g., in multiple, different planes) of the three-dimensional model to provide complementary spatial information regarding a position of the medical device relative to the anatomic structure during a medical procedure performed on the anatomic structure. Such complementary spatial information can, for example, provide spatial context to facilitate controlling the position of the medical device relative to the anatomic structure during the medical procedure.

18 Claims, 8 Drawing Sheets

Related U.S. Application Data continuation of application No. 17/650,830, filed on Feb. 11, 2022, now abandoned, which is a continuation of application No. 17/385,860, filed on Jul. 26, 2021, now abandoned, which is a continuation of application No. 17/144,051, filed on Jan. 7, 2021, now abandoned, which is a continuation of application No. 16/888,490, filed on May 29, 2020, now abandoned.

(58) Field of Classification Search
CPC ............ A61B 2034/2051; A61B 5/062; A61B 2034/2055; A61B 90/37; G06T 15/30; G06T 2210/41; G06T 7/70; G06T 2200/24; G06T 19/00; G06F 3/0346
See application file for complete search history.

(56) References Cited

U.S. PATENT DOCUMENTS

| | | | |
|---|---|---|---|
| 5,391,199 | A | 2/1995 | Ben-Haim |
| 5,433,198 | A | 7/1995 | Desai |
| 5,623,583 | A | 4/1997 | Nishino |
| 5,687,737 | A | 11/1997 | Branham et al. |
| 5,797,849 | A | 8/1998 | Vesely et al. |
| 6,304,267 | B1 | 10/2001 | Sata |
| 6,556,206 | B1 | 4/2003 | Benson et al. |
| 6,664,986 | B1 | 12/2003 | Kopelman et al. |
| 6,961,911 | B2 | 11/2005 | Suzuki et al. |
| 7,315,638 | B2 | 1/2008 | Hara |
| 7,450,749 | B2 | 11/2008 | Rouet et al. |
| 7,656,418 | B2 | 2/2010 | Watkins et al. |
| 7,714,856 | B2 | 5/2010 | Waldinger et al. |
| 7,894,663 | B2 | 2/2011 | Berg et al. |
| 8,014,561 | B2 | 9/2011 | Farag et al. |
| 8,334,867 | B1 | 12/2012 | Davidson |
| 8,784,413 | B2 | 7/2014 | Govari et al. |
| 8,817,076 | B2 | 8/2014 | Steen |
| 2003/0189567 | A1 | 10/2003 | Baumberg |
| 2004/0249809 | A1 | 12/2004 | Ramani et al. |
| 2009/0163810 | A1* | 6/2009 | Kanade .............. A61B 6/5205 600/443 |
| 2009/0281418 | A1 | 11/2009 | Ruijters et al. |
| 2010/0259542 | A1 | 10/2010 | Visser et al. |
| 2011/0236868 | A1 | 9/2011 | Bronstein et al. |
| 2012/0004540 | A1 | 1/2012 | Liu et al. |
| 2012/0245465 | A1 | 9/2012 | Hansegard et al. |
| 2013/0241929 | A1 | 9/2013 | Massarwa et al. |
| 2013/0286012 | A1 | 10/2013 | Medioni et al. |
| 2014/0328524 | A1 | 11/2014 | Hu et al. |
| 2015/0042657 | A1 | 2/2015 | Smith-Casem et al. |
| 2015/0324114 | A1 | 11/2015 | Hurley et al. |
| 2016/0147308 | A1 | 5/2016 | Gelman et al. |
| 2017/0065256 | A1 | 3/2017 | Kim et al. |
| 2017/0265943 | A1* | 9/2017 | Sela .................. A61B 34/20 |
| 2017/0319172 | A1 | 11/2017 | Harlev et al. |

OTHER PUBLICATIONS

ISA, "PCT Application No. PCT/US17/30877 International Search Report and Written Opinion mailed Jul. 14, 2017", 11 pages.
ISA, "PCT Application No. PCT/US17/30928 International Search Report and Written Opinion mailed Jul. 25, 2017", 15 pages.

* cited by examiner

MEDICAL DEVICE VISUALIZATION

CROSS-REFERENCE TO RELATED APPLICATIONS

This application claims the benefit under 35 U.S.C. § 119(e) of U.S. Prov. App. No. 62/330,910, filed May 3, 2016, U.S. Prov. App. No. 62/337,541, filed May 17, 2016, U.S. Prov. App. No. 62/338,068, filed May 18, 2016, U.S. Prov. App. No. 62/357,600, filed Jul. 1, 2016, U.S. Prov. App. No. 62/367,763, filed Jul. 28, 2016, with the entire contents of each of these applications hereby incorporated herein by reference.

This application is also related to the commonly-owned U.S. patent application Ser. No. 15/586,022 (now U.S. Pat. No. 10,475,236), filed May 3, 2017, and entitled "ANATOMICAL MODEL DISPLAYING," the entire contents of which are hereby incorporated herein by reference.

BACKGROUND

Three-dimensional models are used to assist in the placement or use of a device when such placement or use is not easily observable or practical. For example, in medical procedures, three-dimensional models are used to assist in the placement and use of medical devices for the diagnosis or treatment of patients. An example of such a medical procedure carried out with the assistance of a three-dimensional model is the use of a catheter to deliver radio frequency ("RF") ablation to form lesions that interrupt abnormal conduction in cardiac tissue, thus terminating certain arrhythmias in the heart.

SUMMARY

The present disclosure is directed to devices, systems, and methods of presenting multiple images of a three-dimensional model on a graphical user interface to facilitate visualizing the position of a medical device relative to an anatomic structure during a medical procedure. The multiple images can correspond to different views (e.g., in multiple, different planes) of the three-dimensional model to provide complementary spatial information regarding the position of the medical device relative to the anatomic structure during a medical procedure performed on the anatomic structure. Such complementary spatial information can, for example, provide spatial context for controlling the position of the medical device relative to the anatomic structure during the medical procedure. Additionally, or alternatively, one or more of the images can depict a fractional view of the three-dimensional model such that internal and external surfaces of the three-dimensional model are observable on a single graphical user interface as the medical device is moved relative to the anatomic structure during a medical procedure. Thus, for example, the systems and methods of the present disclosure can address visualization challenges associated with certain medical procedures (e.g., cardiac procedures) in which it can be desirable to make observations from a perspective looking into an anatomic structure within which a medical device is positioned.

According to one aspect, a method includes receiving a signal indicative of a medical device in an anatomic structure of a patient, constructing a three-dimensional model including a three-dimensional representation of the anatomic structure and a representation of the medical device relative to the anatomic structure based at least in part on the received location signal, clipping the three-dimensional model based at least in part on the received location signal, and displaying, on a graphical user interface, a first image and a second image. Clipping the three-dimensional model includes removing a first portion of the three-dimensional model relative to a first clipping surface intersecting the three-dimensional model to form a clipped model. The first image includes a projection of the three-dimensional model on a first viewing window of a first image plane, and the second image includes a projection of the clipped model on a second viewing window of a second image plane.

In some implementations, the second image plane can intersect the first image plane.

In certain implementations, the method can further include updating the first image and the second image based on at least one of a user input and a received location signal of the medical device.

In some implementations, the second image plane can be in a fixed orientation relative to the first image plane.

In certain implementations, the three-dimensional representation of the anatomic structure can include a boundary surface and displaying the first image can include displaying a portion of the boundary surface that is not shown in the second image.

In some implementations, clipping the three-dimensional model can further include removing a second portion of the three-dimensional model relative to a second clipping surface, and the clipped model can be substantially between the first clipping surface and the second clipping surface. For example, at least a portion of the first clipping surface and the second clipping surface are substantially parallel to one another.

In certain implementations, the first clipping surface can be a plane. For example, the first clipping surface can be substantially parallel to the second image plane.

In some implementations, constructing the three-dimensional model can include receiving one or more images of the anatomic structure and registering the images to a coordinate system of a sensor providing the signal indicative of the location of the medical device.

In some implementations, constructing the three-dimensional model can include updating the representation of the medical device based on the received location signal. For example, the first clipping surface can extend through the updated representation of the medical device.

In certain implementations, the received location signal can be a time-varying signal and clipping the three-dimensional model can further include processing the time-varying received location signal and selecting the first clipping surface based on the processed, received location signal. For example, processing the time-varying received location signal can include low-pass filtering the received location signal.

In certain implementations, the second image can include a projection of the clipped model extending in a direction from the second viewing window, toward the three-dimensional model, and substantially orthogonal to the second image plane.

In some implementations, the three-dimensional model can include a boundary surface of the anatomic structure and a portion of the boundary surface in the clipped model in the second image is more translucent than a corresponding portion of the boundary surface in the three-dimensional model in the first image.

In certain implementations, the three-dimensional model can include a boundary surface of the anatomic structure and displaying the second image can include highlighting a contour of the boundary surface within a predetermined distance of the first clipping surface. For example, highlighting the contour of the boundary surface within the predetermined distance of the first clipping surface includes highlighting a contour of the boundary surface intersected by the first clipping surface.

In some implementations, displaying the first image and the second image can include displaying the first image and the second image simultaneously on the graphical user interface.

In certain implementations, an included angle between the second image plane and the first image plane is less than or equal to 90 degrees and greater than about 60 degrees. For example, the second image plane can be orthogonal to the first image plane.

In some implementations, the method can further include adjusting the first image plane and maintaining the second image plane in a fixed orientation relative to the first image plane. Additionally, or alternatively, the second image plane can be restricted to a direction superior to the representation of the location of the medical device in the three-dimensional model. Further. or instead, adjusting the first image plane can include orienting the first image plane relative to the location, in the anatomic structure of the patient, of the medical device.

In certain implementations, displaying the first image and the second image on the graphical user interface can include displaying the first image as larger than the second image.

In some implementations, displaying the first image and the second image on the graphical user interface can include adjusting the size of the three-dimensional model as projected onto one or both of the first viewing window and the second viewing window.

In certain implementations, displaying the first image and the second image on the graphical user interface can include adjusting a distance from at least one of the first image plane or the second image plane to the three-dimensional model.

In some implementations, displaying the first image and the second image can include sizing at least one of the first viewing window or the second viewing window. For example, sizing the first viewing window can be based on at least one dimension of the three-dimensional model in the first image plane. Additionally, or alternatively, sizing the second viewing window can be based on a bounding volume defined around the three-dimensional model. As an example, sizing the second viewing window can include sizing the second viewing window based on a dimension (e.g., a maximum dimension) of the bounding volume. Further, or instead, the bounding volume can be a sphere (e.g., a sphere having a diameter based on a maximum dimension of the three-dimensional model).

In certain implementations, the method can further include receiving a signal indicative of a location of a treatment applied by the medical device to the anatomic structure. In certain instances, constructing the three-dimensional model can include adding visual indicia to the three-dimensional model, the visual indicia corresponding to the location of the treatment, and at least one of the first image and the second image including the visual indicia.

In some implementations, the method can further include receiving a signal indicative of a location of an anatomic feature of the anatomic structure. In some instances, constructing the three-dimensional model can include adding visual indicia to the three-dimensional model, the visual indicia corresponding to the location of the anatomic feature, and the first image and the second image each including the visual indicia.

In certain implementations, the second image can include visual indicia highlighting a boundary of the medical device. For example, the visual indicia highlighting the boundary of the medical device can vary in color according to one or more of time and around the boundary of the medical device.

According to another aspect, a non-transitory, computer-readable storage medium has stored thereon computer executable instructions for causing one or more processors to receive a signal indicative of a location of a medical device in an anatomic structure of a patient, construct a three-dimensional model including a three-dimensional representation of the anatomic structure and a representation of the medical device relative to the anatomic structure based at least in part on the received location signal, clip the three-dimensional model based at least in part on the received location signal, and display, on a graphical user interface, a first image and a second image. Clipping the three-dimensional model includes removing a first portion of the three-dimensional model relative to a first clipping surface intersecting the three-dimensional model to form a clipped model. The first image includes a projection of the three-dimensional model on a first viewing window of a first image plane, and the second image includes a projection of the clipped model on a second viewing window of a second image plane.

According to yet another aspect, a method includes receiving a signal indicative of a location of a medical device in an anatomic structure of a patient, updating a three-dimensional model based at least in part on the received location signal, forming a first image including a projection (on a first viewing window of a first image plane) of at least one portion of the updated three-dimensional model, forming (on a second viewing window of a second image plane) a second image of another portion of the updated three-dimensional model, and displaying, on a graphical user interface, the first image and the second image. The portion of the three-dimensional model projected on the second viewing window is less than the at least one portion of the updated three-dimensional model projected on the first viewing window, and the second image plane intersects the first image plane. The three-dimensional model includes a three-dimensional representation of the anatomic structure and a representation of the medical device relative to the anatomic structure.

In some implementations, the method further includes adjusting the first image plane and maintaining the second image plane in a fixed orientation relative to the first image plane. For example, adjusting the first image plane can include orienting the first image plane relative to the received location signal. Additionally, or alternatively, orienting the first image plane relative to the received location signal can include orienting the first image plane in a direction perpendicular to a weighted sum of surface normal vectors along a portion, closest to the medical device, of a boundary surface of the anatomic structure in the three-dimensional model.

In certain implementations, displaying the first image and the second image can include displaying the first image and the second image simultaneously on the graphical user interface.

In some implementations, the second image plane can be orthogonal to the first image plane.

According to still another aspect, a system includes a catheter and a catheter interface unit. The catheter has a distal portion and a proximal portion. The distal portion is mechanically coupled to the proximal portion, and the distal portion is insertable into a chamber of a patient's heart and movable within the chamber via manipulation of the proximal portion. The catheter interface unit is in electrical communication with the catheter and includes a graphical user interface, one or more processors, and a non-transitory, machine-readable storage medium having stored thereon machine executable instructions for causing the one or more processors to receive a signal indicative of a location of the distal portion of the catheter in the chamber of the patient's heart, based at least in part on the received location signal, update a three-dimensional model, the three-dimensional model including a three-dimensional representation of the heart chamber and a representation of the catheter relative to the heart chamber, and display a first image and a second image on the graphical user interface, wherein the first image includes a projection of the updated three-dimensional model to a first viewing window of a first image plane, and the second image includes a projection of a portion of the updated three-dimensional model on a second viewing window of a second image plane, the second image plane intersecting the first image plane, and the portion of the updated three-dimensional model displayed in the second viewing window being less than the entirety of the three-dimensional model displayed on the first viewing window.

In certain implementations, the second image plane can have a fixed orientation relative to the first image plane. For example, the second image plane can be orthogonal to the first image plane.

In some implementations, the instructions to display the first image can include instructions to adjust the first image plane based on the received location signal. For example, the instructions to adjust the first image plane can include instructions to adjust the first image plane to an orientation perpendicular to a weighted sum of surface normal vectors along a portion, closest to the distal portion of the catheter, of a boundary surface of the chamber of the heart in the three-dimensional model.

Implementations can include one or more of the following advantages.

In certain implementations, displaying a first image and a second image on the graphical user interface can include displaying a projection of the three-dimensional model on a first viewing window of the first image plane and displaying the projection of only a determined portion of the three-dimensional model on a second viewing window of the second image plane. It should be appreciated that displaying the three-dimensional model in one perspective and a displaying only a portion of the three-dimensional model in another perspective can provide complementary views of the medical device that can be useful for maneuvering the medical device in three-dimensions. Additionally, or alternatively, such multiple perspectives can facilitate visualization from a perspective looking into a surface of an anatomic structure within which the medical device is positioned while providing a perspective useful for navigation of the medical device relative to the surface of the anatomic structure.

In some implementations, a second image plane can extend through a representation of the medical device and the determined portion of the three-dimensional model can extend in a direction away from the second image plane. In such implementations, a corresponding second image can be unobstructed by the three-dimensional representation of the anatomic structure, thus facilitating visualization of the medical device relative to a surface of the anatomic structure.

In certain implementations, a first image and a second image can be updated based on a received signal indicative of a location of a medical device in an anatomic structure. Accordingly, the first image and the second image can provide the physician with dynamically changing information about the position of the medical device relative to the anatomic structure during the medical procedure. Thus, for example, the first image and the second image can be useful for providing the physician with substantially real-time guidance for maneuvering the medical device during the medical procedure.

Other aspects, features, and advantages will be apparent from the description and drawings, and from the claims.

BRIEF DESCRIPTION OF THE DRAWINGS

Like reference symbols in the various drawings indicate like elements.

DETAILED DESCRIPTION

The present disclosure is generally directed to devices, systems, and methods of controlling, on a graphical user interface, multiple display views of a medical device relative to an anatomic structure of a patient during a medical procedure being performed on the anatomic structure of the patient. For example, the systems and methods of the present disclosure can be used to provide spatial context to a physician to facilitate multi-directional positioning of the medical device relative to the anatomic structure during the medical procedure. By way of non-limiting example and for the sake of clarity of explanation, certain aspects of the present disclosure are described with respect to visualization of a cardiac catheter inserted into a heart cavity as part of a diagnostic and/or treatment procedure. However, it should be appreciated that, unless otherwise specified or made clear from the context, the systems and methods of the present disclosure can be used for any of various different medical procedures in which a three-dimensional model of an anatomic structure (e.g., a hollow anatomic structure) is used to visualize a position of a medical device in the hollow anatomic structure during the medical procedure. For example, the systems and methods of the present disclosure can, additionally or alternatively, be used in interventional pulmonology, brain surgery, and/or sinus surgery (e.g., sinuplasty).

As used herein, the term "physician" can include any type of medical personnel who may be performing or assisting a medical procedure. The term "medical procedure" can include any manner and type of medical procedure and, therefore, should be considered to include any and all manner and forms of diagnosis and treatment, unless otherwise specified or made clear from the context.

As used herein, the term "patient" should be considered to include any mammal, including a human, upon which a medical procedure is being performed.

Figure 1:
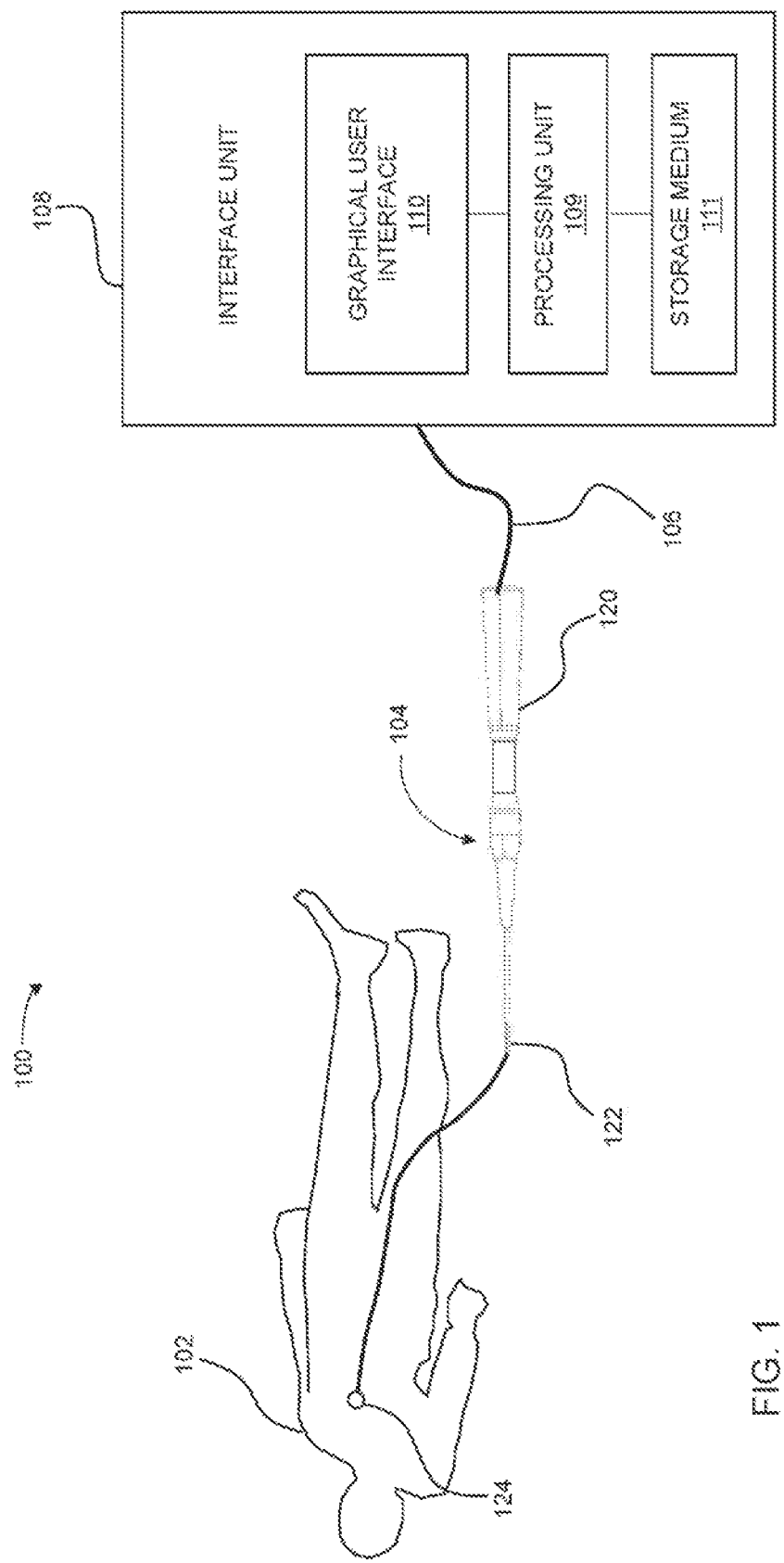
FIG. 1 is a schematic representation of a system during a medical procedure being performed on a patient.

FIG. 1 is a schematic representation of a system 100 during a medical procedure (e.g., an ablation treatment) being performed on a patient 102. The system 100 can include a catheter 104 connected via an extension cable 106 to an interface unit 108. The interface unit 108 (e.g., a catheter interface unit) can include a processing unit 109 (e.g., one or more processors), a graphical user interface 110, and a storage medium 111. The graphical user interface 110 and the storage medium 111 can be in electrical communication (e.g., wired communication, wireless communication, or both) with the processing unit 109.

As described in further detail below, the graphical user interface 110 can be used as part of diagnosis and/or treatment of cardiac tissue of the patient 102 by, for example, displaying multiple images, with each image corresponding to a different perspective of a three-dimensional model during a medical procedure. As compared to systems providing a display of only a single image of a three-dimensional model, displaying multiple, different views of the three-dimensional model on the graphical user interface 110 according to any one or more of the methods described herein can provide a physician with improved spatial context for three-dimensional movement of the catheter 104 relative to one or more surfaces of the anatomic structure. As a specific example related to an exemplary treatment, displaying multiple, different images of the three-dimensional model on the graphical user interface 110 according to any one or more of the methods described herein can facilitate three-dimensional movement of the catheter 104 within the anatomic structure to create one or more lesions in a desired pattern on one or more surfaces of the anatomic structure represented by the three-dimensional model.

As also described in greater detail below, the multiple images displayed on the graphical user interface can be based on a received location of the catheter 104 in the heart cavity. Accordingly, the multiple images can be updated (e.g., automatically) as the location of the catheter 104 changes during a medical procedure. Such dynamic updates to the multiple images can, in turn, be useful for providing the physician with updated views of the three-dimensional model in the vicinity of the catheter 104, facilitating both fine and coarse adjustments to the position of the catheter 104 relative to a surface of the anatomic structure.

Figure 2:
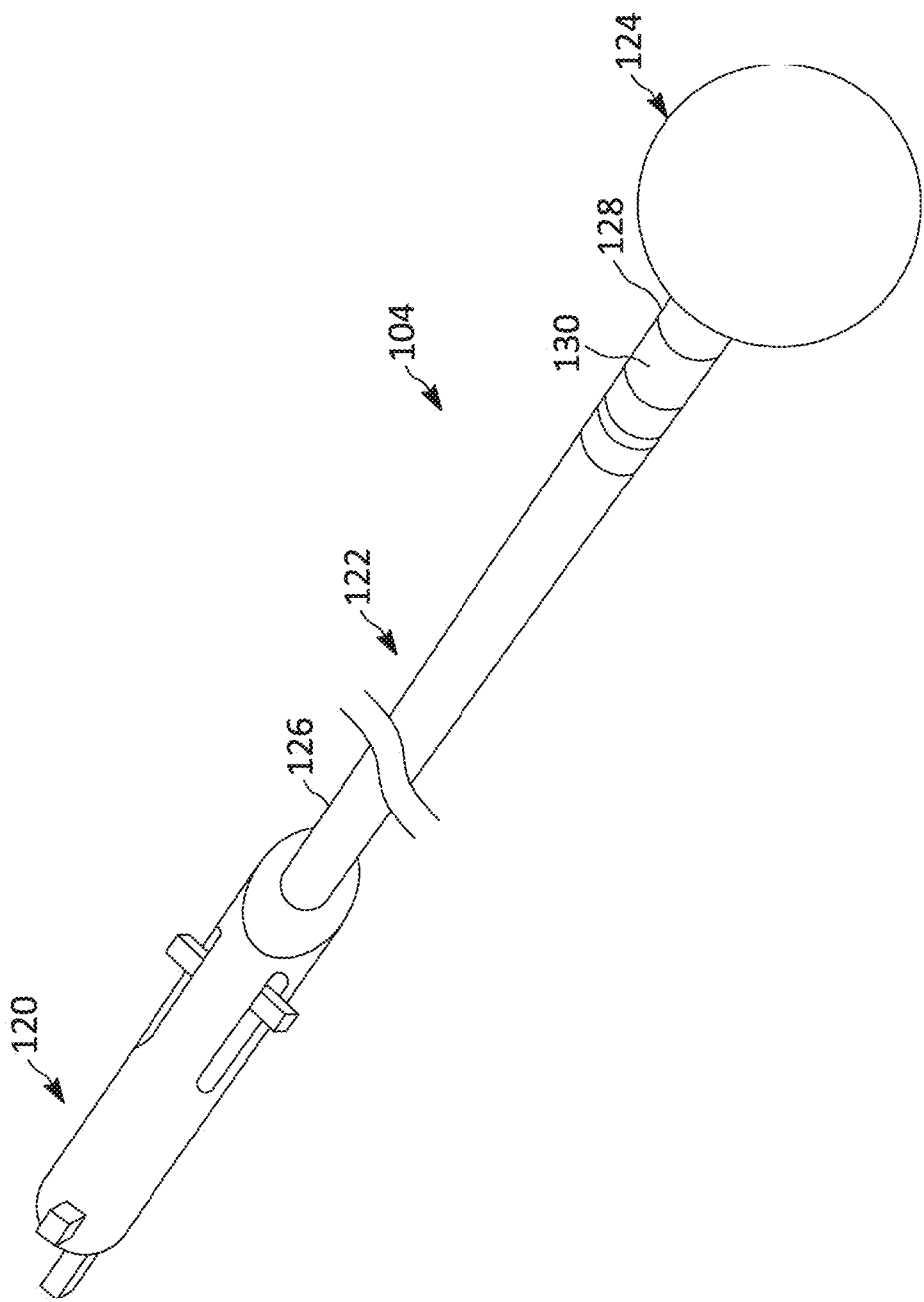
FIG. 2 is a perspective view of a catheter of the system of FIG. 1.
Figure 3:
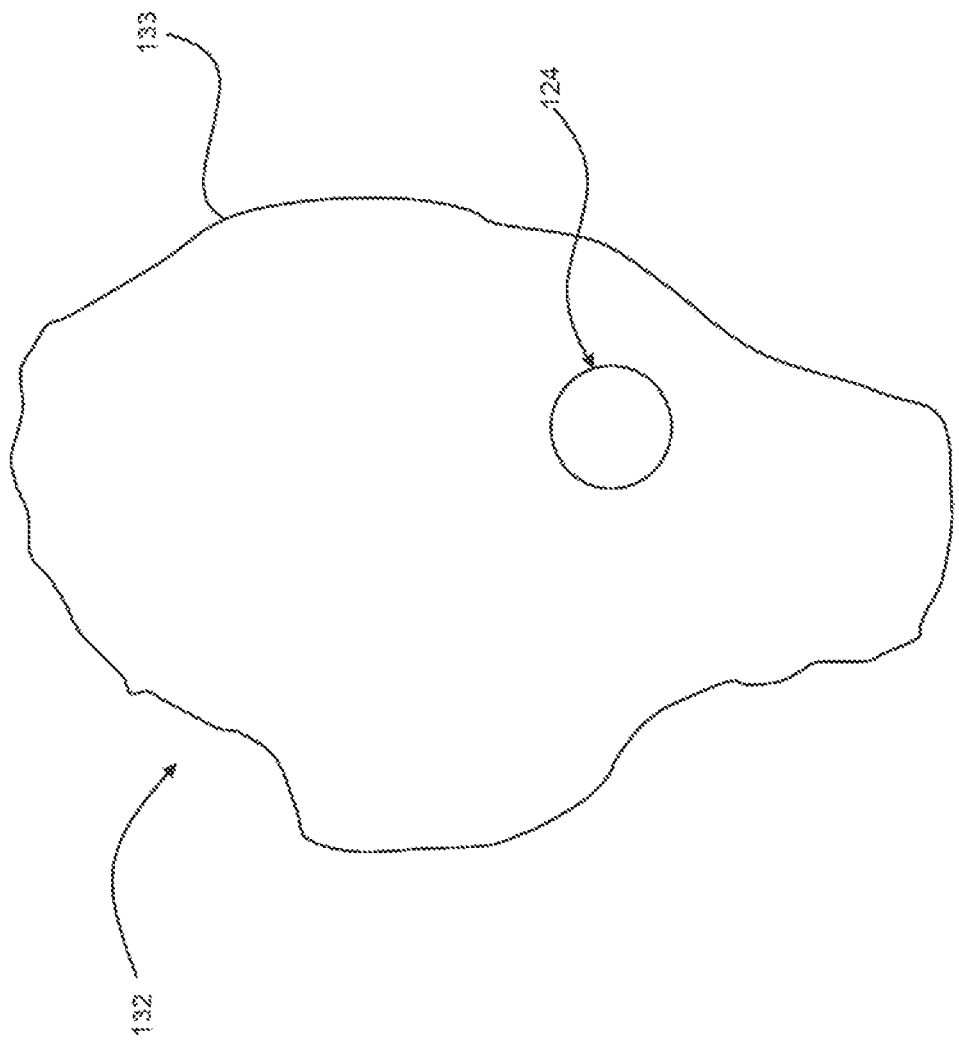
FIG. 3 is a schematic representation of a tip section of the catheter of FIG. 1 disposed in an anatomic cavity during the medical procedure associated with FIG. 1.

Referring to FIGS. 1 and 2, the catheter 104 can be any of various different catheters known in the art (e.g., for diagnosis, treatment, or both). Thus, the catheter 104 can include a handle 120, a catheter shaft 122, and a tip section 124. The catheter shaft 122 can include a proximal portion 126 secured to the handle 120, and a distal portion 128 coupled to the tip section 124.

The tip section 124 generally includes any portion of the catheter 104 that directly or indirectly engages tissue for the purpose of treatment, diagnosis, or both and, therefore, can include all manner and type of contact and/or non-contact interaction with tissue known in the art. For example, the tip section 124 can include contact and/or non-contact interaction with tissue in the form of energy interaction (e.g., electrical energy, ultrasound energy, light energy, and any combinations thereof) and further, or instead, can include measurement of electrical signals emanating from tissue. Thus, for example, the tip section 124 can deliver energy (e.g., electrical energy) to tissue in the anatomic structure as part of any number of procedures including treatment, diagnosis, or both.

In certain implementations, the delivery of energy from the tip section 124 to the tissue can be through direct contact between the tip section 124 and the tissue. In such implementations, it may be particularly desirable for the graphical user interface 110 to display multiple, different images of the three-dimensional model to provide the physician with knowledge of the position of the tip section 124 relative to one or more surfaces of the anatomic structure. It should be further appreciated that the systems and methods of the present disclosure can be implemented using any number and manner of designs of the catheter 104 that rely upon, or at least derive some benefit from, knowledge of location of the tip section 124 relative to one or more surfaces of the anatomic structure.

The catheter 104 can further include a magnetic position sensor 130 along the distal portion 128 of the catheter shaft 122. The magnetic position sensor 130 can be any of various magnetic position sensors well known in the art and can be positioned at any point along the distal portion 128. The magnetic position sensor 130 can, for example, include one or more coils that detect signals emanating from magnetic field generators. One or more coils for determining position with five or six degrees of freedom can be used. The magnetic field detected by the magnetic position sensor 130 can be used to determine the position and/or orientation of the distal portion 128 of the catheter shaft 122 according to one or more methods commonly known in the art such as, for example, methods based on using a magnetic sensor, such as the magnetic position sensor 130, to sense magnetic fields and using a look-up table to determine location of the magnetic position sensor 130. Accordingly, because the tip section 124 is coupled to the distal portion 128 of the catheter shaft 122 in a known, fixed relationship to the magnetic position sensor 130, the magnetic position sensor 130 can also provide the location of the tip section 124. While the location of the tip section 124 is described as being determined based on magnetic position sensing, other position sensing methods can additionally or alternatively be used. For example, the location of the tip section 124 can be additionally, or alternatively, based on impedance, ultrasound, and/or imaging (e.g., real time MRI or fluoroscopy).

Referring to FIGS. 1-5, a three-dimensional representation 134 of an anatomic cavity 132 (e.g., an anatomic structure such as a heart cavity) of the patient 102 can be built based on known positions of the tip section 124 of the catheter 104 in the anatomic cavity 132 (e.g., prior to application of an ablation treatment or other type of treatment) and additionally, or alternatively, based on images of the anatomic cavity 132 acquired prior to or during the procedure, as described in greater detail below. For example, if the tip section 124 of the catheter 104 is movable in blood in the anatomic cavity 132 and obstructed only by a surface 133 of the anatomic cavity 132, the known positions of the tip section 124 of the catheter 104 can be taken together to provide an indication of a blood-tissue boundary of the anatomic cavity 132, and this blood-tissue boundary can form a basis for the three-dimensional representation 134 of the anatomic cavity 132.

In general, a three-dimensional model 136 projected onto the graphical user interface 110 can include the three-dimensional representation 134 of the anatomic cavity 132 and a representation 138 of the catheter 104. The representation 138 of the catheter 104 can include, for example, a depiction of the tip section 124, at the position of the tip section 124 determined based on the signal from the magnetic position sensor 130. Examples of such a depiction of the tip section 124 can include, by way of example and not limitation, one or more of the following: an icon; an outline; a two-dimensional geometric shape such as a circle; and a three-dimensional geometric shape such as a sphere. Additionally, or alternatively, the representation 138 of the catheter 104 can include a three-dimensional depiction of the tip section 124. Continuing with this example, the three-dimensional depiction of the tip section 124 can be at least partially based on knowledge of the size and shape of the tip section 124. Thus, for example, in implementations in which the tip section 124 is deformed through contact with a surface of an anatomic structure, the deformation of the tip section 124 can be shown in the three-dimensional depiction.

It should be appreciated that the three-dimensional model 136 has utility as, among other things, an analog for the position of the tip section 124 of the catheter 104 in the anatomic cavity 132. That is, the position of the tip section 124 of the catheter 104 relative to the surface 133 of the anatomic cavity 132 is known (e.g., based on the signal received by the interface unit 108 from the magnetic position sensor 130) and can be represented on the graphical user interface 110 as a position of the representation 138 of the catheter 104 relative to the three-dimensional representation 134 of the anatomic cavity 132. Thus, for example, as the tip section 124 moves within the anatomic cavity 132 during a medical procedure, the representation 138 of the catheter 104 can be depicted on the graphical user interface 110 as undergoing analogous, or at least similar, movements relative to the three-dimensional representation 134 of the anatomic cavity 132 in the three-dimensional model 136. Given this correspondence between the three-dimensional model 136 and the physical aspects of the medical procedure, it should be appreciated that displaying multiple images of the three-dimensional model 136 on the graphical user interface 110 can be a useful visualization tool for the physician as the physician moves the tip portion 124 of the catheter 104 in the anatomic cavity 132.

In an exemplary treatment, the tip section 124 can be placed into contact with the surface of the anatomic cavity 132 and RF energy can be directed from the tip section 124 to the surface 133 of the anatomic cavity 132 to ablate tissue at some depth relative to the surface 133. In implementations in which the anatomic cavity 132 is a heart cavity, such ablations created by the tip section 124 along the surface 133 of the anatomic cavity 132 can, for example, treat cardiac arrhythmia in patients with this condition. However, the effectiveness of the ablations created using the tip section 124 along the surface 133 of such a heart cavity can be dependent upon location of the ablations. Accordingly, the multi-dimensional visualization of the position of the catheter 104 facilitated by displaying multiple images of the three-dimensional model 136, according to any one or more of the methods described herein, can be useful for the efficient and effective mapping of the heart and/or efficient and effective delivery of ablation treatment to treat cardiac arrhythmia.

The graphical user interface 110 can be two-dimensional such that projections of the three-dimensional model 136 can be displayed on the graphical user interface 110 according to any one or more of the methods described in greater detail below. Thus, for example, the graphical user interface 110 can be a display of a two-dimensional monitor of any of various different known types. It should be appreciated, however, that the graphical user interface 110 can additionally or alternatively include a three-dimensional display including, for example, an augmented reality environment and/or a virtual reality environment. In general, multiple instances of all or a portion of the three-dimensional model 136 can be displayed on the graphical user interface 110, with each instance corresponding to a view useful for providing the physician with spatial context (e.g., through reference points viewed from multiple, different perspectives) for three-dimensional maneuvering of the tip portion 124 in the anatomic cavity 132.

Figure 5:
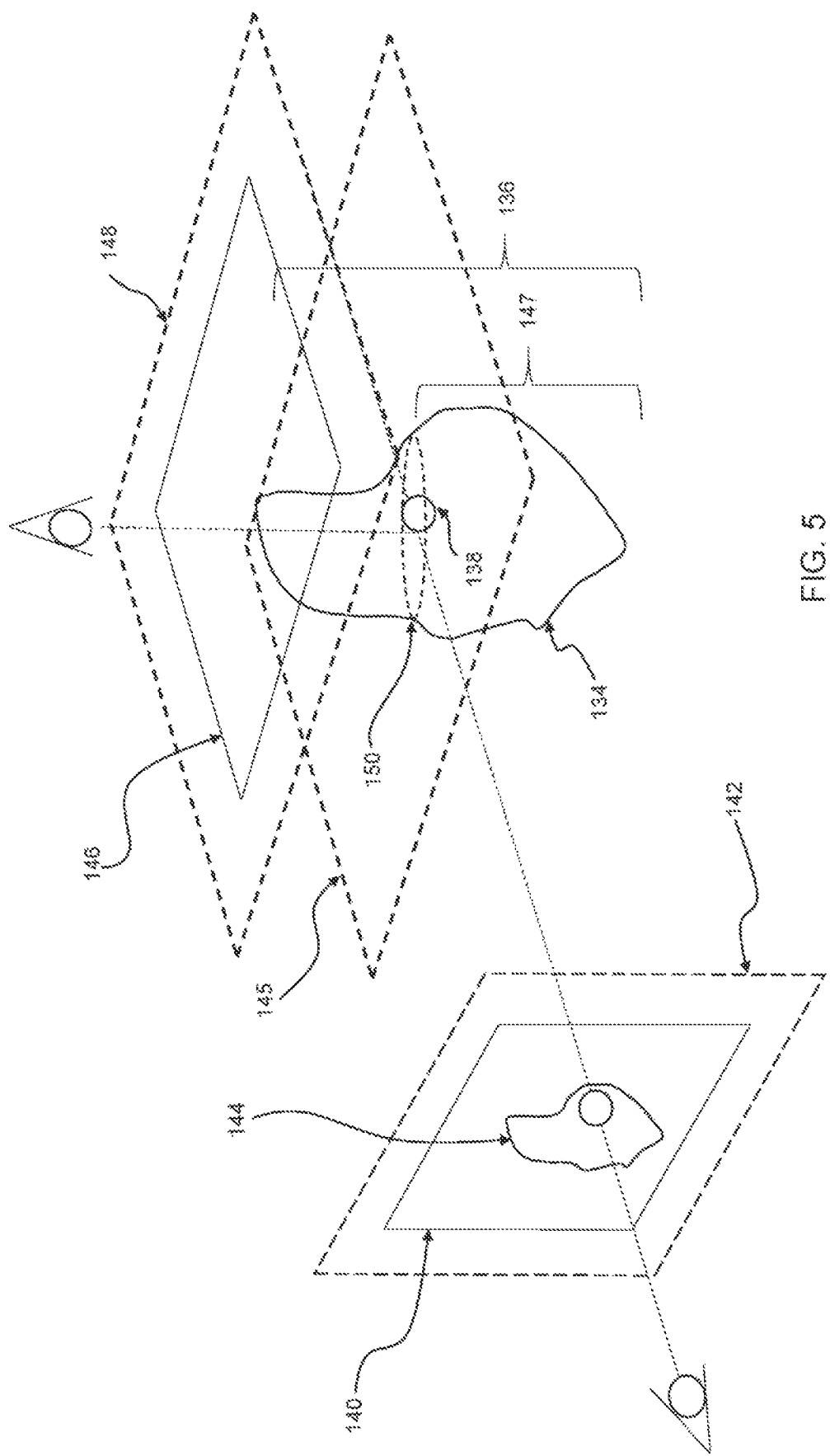
FIG. 5 is a schematic representation of the projections of the three-dimensional model of FIG. 4 onto the first viewing window and the second viewing window of the graphical user interface of FIG. 4.

In instances in which the graphical user interface 110 is a two-dimensional display, the three-dimensional model 136 can be projected in multiple directions to form multiple, two-dimensional images displayed on the graphical user interface 110. For example, as shown in FIG. 5, the three-dimensional model 136 can be projected to a first viewing window 140 of a first image plane 142 to form a first image 144 and to a second viewing window 146 of a second image plane 148 to form a second image 150. The first viewing window 140 can correspond to a field of view of a portion of the graphical user interface 110, upon which the first image 144 is displayed. Similarly, the second viewing window 146 can correspond to a field of view of another portion of the graphical user interface 110, upon which the second image 150 is displayed.

The first image plane 142 is different from the second image plane 148 such that the resulting display of the first image 144 and the second image 150 on the two-dimensional display of the graphical user interface 110 represents the three-dimensional model 136 from different perspectives. As described in greater detail below, the second image plane 148 can be positioned relative to the three-dimensional model 136 and a clipping surface 145 such that the projection of the three-dimensional model 136 forming the second image 150 shows a clipped portion of the three-dimensional model 136 as projected onto the second viewing window 146. The first image 144 can show the entirety of the three-dimensional model 136 projected onto the first viewing window 140. Thus, more generally, the first image 144 and the second image 150 can provide visual representations of multiple, different surfaces of the three-dimensional representation 134 of the anatomic cavity 132, with the first image 144 showing more of the three-dimensional model (e.g., the entirety of the three-dimensional model) than is shown in the second image 150. Accordingly, in combination, the first image 144 and the second image 150 can facilitate observation of one or more spatial reference points from multiple perspectives to provide the physician with spatial context useful for maneuvering the tip section 124 in three-dimensions in the anatomic cavity 132.

In general, the clipping surface 145 can extend through the three-dimensional model 136 to divide the model into two portions. For example, the clipping surface 145 can extend through the three-dimensional representation 134 of the anatomic structure 132 and, optionally, through the representation 138 of the catheter 104. One of the portions of the three-dimensional model 136 can be removed relative to the clipping surface 145 to form a clipped model 147. As a specific example, the portion of the three-dimensional model 136 on one side of the clipping surface 145 can be removed to form the clipped model 147. As used herein, removing a portion of the three-dimensional model 136 to form the clipped model 147 can include any manner and form of deleting, replacing, deemphasizing (e.g., making translucent), or otherwise rendering the portion of the three-dimensional model 136 in the clipped model 147 as distinguished from the portion of the three-dimensional model 136 that is not in the clipped model 147. The point of view of the second viewing window 146 can intersect the clipping surface 145 such that the second image 150 can include a visual representation of a region within a boundary surface defined by the three-dimensional model 136. By way of a more specific example, the clipping surface 145 can be a plane, and the second image plane 148 defining the second viewing window 146 can be substantially parallel to the clipping surface 145. While clipping surface 145 can be usefully formed as a plane to facilitate visualization into the boundary surface defined by the three-dimensional model, it should be appreciated that the clipping surface 145 can have any of various difference shapes including, for example, one or more curved surfaces, a series of planar surfaces, and combinations thereof.

The clipping surface 145 can be substantially fixed relative to the second image plane 148. In such implementations, it should be understood that the clipping surface 145 can move as the second image plane 148 moves. This can advantageously produce dynamic changes the clipped model 147 in coordination with the second image plane 148. The result, therefore, of such dynamic changes is that the second image 150 can change as the second image plane 148 moves, as described in further detail below.

Additionally, or alternatively, the clipping surface 145 can be adjustable relative to the second image plane 148. For example, the clipping surface 145 can be adjustable based on one or more user inputs related to one or more of the shape and positioning of the clipping surface relative to the second image plane 148. Such adjustability can be useful, for example, for facilitating observation of specific portions of the three-dimensional model 136. One or more features (e.g., point-of-view and size) of the first image 144 displayed on the graphical user interface 110 can be a function of at least the position of the first image plane 142 relative to the three-dimensional model 136 and the size and position of the first viewing window 140 on the first image plane 142. Similarly, one or more features of the second image 150 displayed on the graphical user interface 110 can be a function of at least the position of the second image plane 148 relative to the three-dimensional model 136 and the size and position of the second viewing window 146 on the second image plane 148. As the tip section 124 is moved within the anatomic cavity 132, the position of one or both of the first image plane 142 and the second image plane 148 can change relative to the three-dimensional model 136 and, additionally, or alternatively, the size and position of one or both of the first viewing window 140 and the second viewing window 146 on the respective one of the first image plane 142 and the second image plane 148 can change. The result of such changes can include corresponding changes to the point-of-view and/or size of a respective one of the first image 144 and the second image 150 displayed on the graphical user interface 110.

At any of various different time steps, the orientation of the first image plane 142 can be adjusted relative to the three-dimensional model 136. As an example, adjusting the first image plane 142 can be based on the location of the catheter 104 in the anatomic cavity 132 of the patient 102.

Continuing with this example, the orientation of the second image plane 148 can be determined based on the orientation of the first image plane 142 such that both the first image plane 142 and the second image plane 148 are adjusted relative to the three-dimensional model 136 based on the location of the catheter 104 in the anatomic cavity 132 of the patient 102. It should be appreciated that adjustment of one or both of the first image plane 142 and the second image plane 148 based on the location of the catheter 104 in the anatomic cavity 132 can be useful for providing dynamically changing views of the three-dimensional model 136 shown in the first image 144 and the second image 150 displayed on the graphical user interface 110. Any of various different aspects of forming the first image 144 and/or the second image 150 displayed on the graphical user interface 110 can be filtered such that the dynamically changing views of the three-dimensional model 136 shown in the respective first image 144 and the second image 150 can be shown as undergoing smooth motion. For example, smooth transitions of one or both of the first image 144 and the second image 150 can be achieved by filtering one or more of the following the location of the catheter 104 in the anatomic cavity 132, adjustment of one or both of the first image plane 142 and the second image plane 148, and adjustment of one or both of the first viewing window 140 and the second viewing window 146.

In certain implementations, the second image plane 148 can be in a fixed orientation (e.g., at a fixed angle) relative to the first image plane 142. In such implementations, the position of the first image plane 142 can be adjusted relative to the three-dimensional model 136 while the second image plane 148 remains in a fixed orientation relative to the first image plane 142, thus producing a fixed change in the second image 150 when the first image 144 changes on the graphical user interface 110. Such fixed orientation of the second image plane 148 relative to the first image plane 142 can be useful, in certain instances, for providing a fixed reference for the second image 150. With such a fixed reference for the second image 150, the physician can combine the information presented in the first image 144 and the second image 150 by tracking only a single coordinate system.

While the second image plane 148 can be in a fixed orientation relative to the first image plane 142, other implementations are additionally or alternatively possible. For example, an included angle between the first image plane 142 and the second image plane 148 can be variable (e.g., between a range of angles). As a more specific example, the included angle between the first image plane 142 and the second image plane 148 can be an input provided by the physician according, for example, to a visualization preference of the physician.

Whether in a fixed or variable orientation relative to one another, an included angle between the second image plane 148 and the first image plane 142 can be less than or equal to 90 degrees and greater than about 60 degrees. Thus, for example, in implementations in which the second image plane 148 is in a fixed orientation relative to the first image plane 142, the second image plane 148 can be substantially orthogonal to the first image plane 142. Such a substantially orthogonal orientation of the second image plane 148 relative to the first image plane 142 can be useful, for example, for providing the physician with a fixed coordinate system with which to compare the first image and the second image and, thus, appreciate spatial context provided by the combination of the first image and the second image.

In some implementations, the second image plane 148 can be restricted to a specific orientation relative to the three-dimensional model 136. As an example, the second image plane can be restricted to a direction superior to the representation of the catheter 104 included in the three-dimensional model 136 such that the second image 150 corresponding to the second image plane 148 is in a fixed orientation relative to the catheter 104. Such fixed orientation of the second image plane 148 relative to the representation of the catheter 104 can facilitate, in certain instances, locating a specific portion (e.g., an ablation electrode) of the catheter 104 relative to one or more surfaces of the anatomic cavity 132 represented in the three-dimensional model 136.

Figure 6:
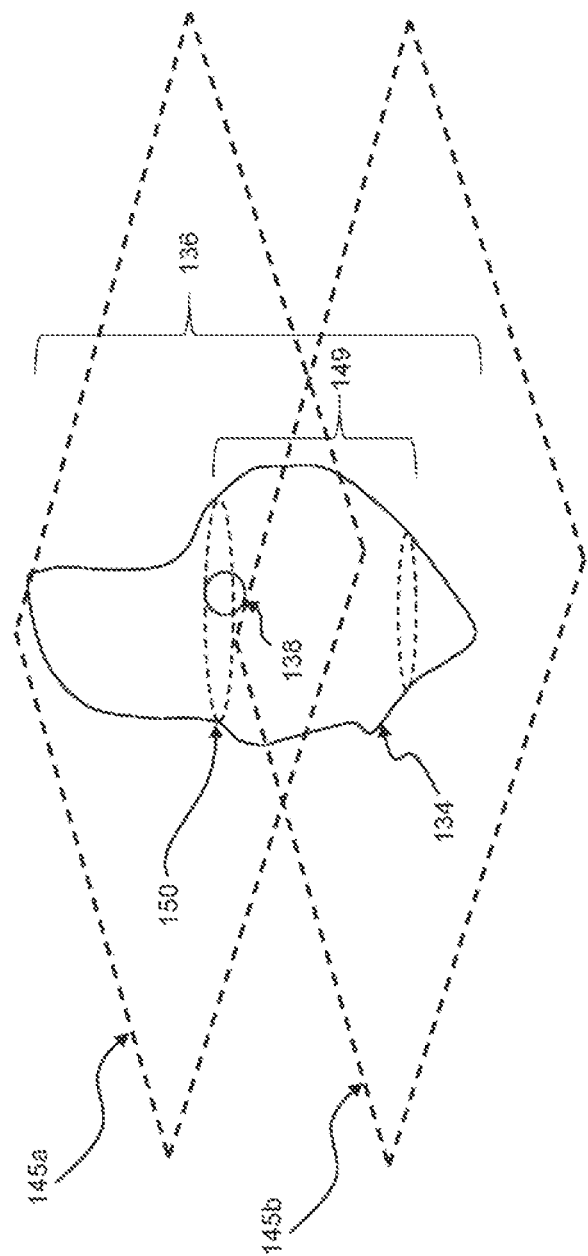
FIG. 6 is a schematic representation of two clipping surfaces slicing the three-dimensional model of FIG. 4.

While a single clipping surface is depicted in FIG. 5 for the sake of clarity of illustration and explanation, it should be appreciated that multiple clipping surfaces can be used to remove portions of three-dimensional model as necessary to facilitate visualization of one or more aspects of the three-dimensional model. For example, as shown in FIG. 6, a first clipping surface 145a and a second clipping surface 145b each intersect the three-dimensional model 136. A portion of the three-dimensional model 136 relative to the first clipping surface 145a can be removed. Similarly, a portion of the three-dimensional model 136 relative to the second clipping surface 145b can be removed. With the portions of the three-dimensional model 136 removed, the clipped model is a slice 149. In general, the slice 149 can be projected onto a viewing window (e.g., the second viewing window 146 in FIG. 5) according to any one or more of the various methods described herein. The projection of the slice 149 onto a viewing window can be useful, for example, for representing complex anatomic geometry and, thus, for providing a physician with useful views of an anatomic structure (e.g., the anatomic structure 132 in FIG. 3).

Figure 7:
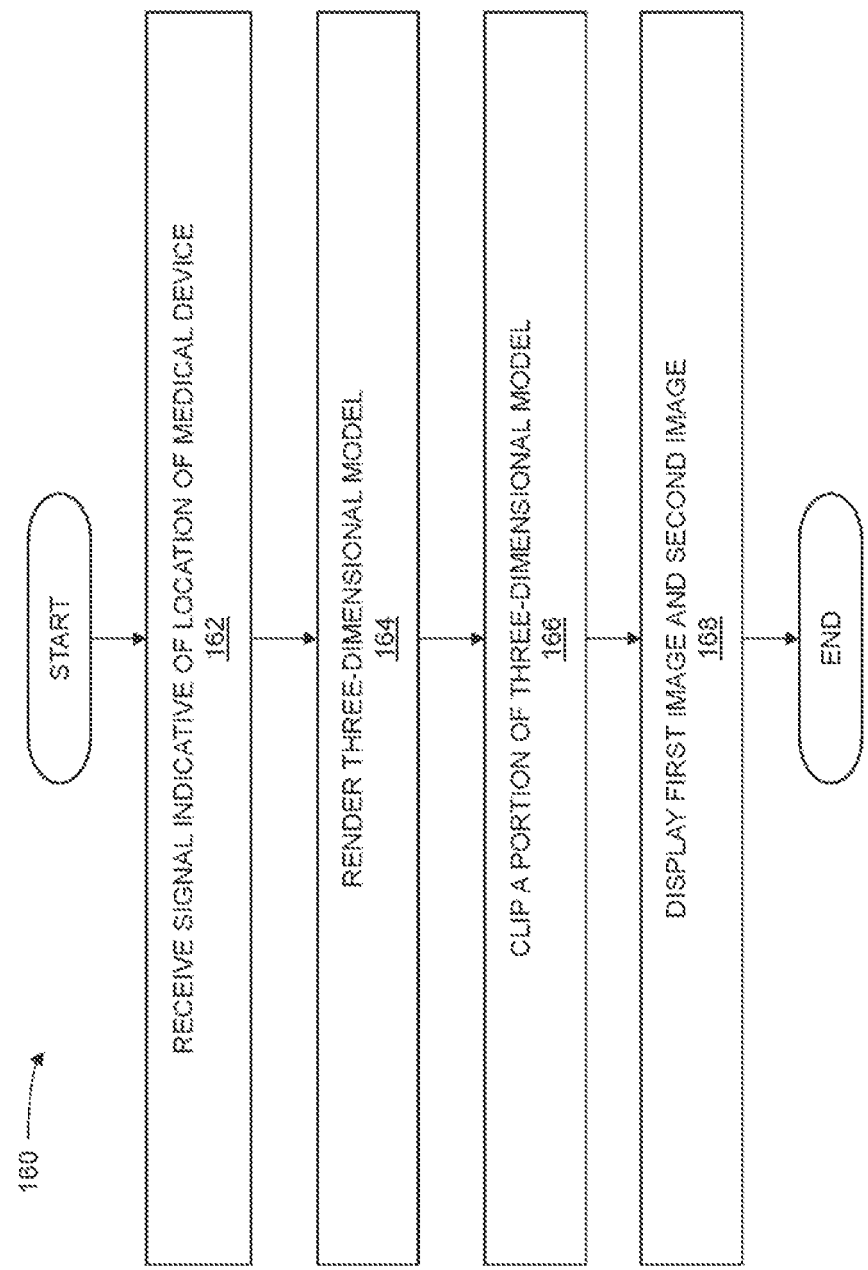
FIG. 7 is a flowchart of an exemplary method of displaying multiple images of a three-dimensional model on a graphical user interface.

In general, unless otherwise indicated, each of the following exemplary methods can be implemented using the system 100 (FIG. 1) and/or one or more components thereof. Thus, it should be understood that the three-dimensional model 136 can be stored in a memory such as the storage medium 111 (FIG. 1). It should be further or alternatively understood that projection of the three-dimensional model 136 to form the first image 144 and the second image 150 on the graphical user interface 110, according to any one or more of the methods described herein, can be carried out by the processing unit 109 (FIG. 1) executing computer-executable instructions stored on the storage medium 111 (FIG. 1). The instructions stored on the storage medium 111 and executable by the processing unit 109 to display the first image 144 and the second image 150 of the three-dimensional model 136 can be, for example, an application built using Visualization Toolkit, an open-source 3D computer graphics toolkit, available at www.vtk.org. FIG. 7 is a flowchart of an exemplary method 160 of displaying multiple images of a three-dimensional model on a graphical user interface. In addition to or as an alternative to facilitating visualization in a heart chamber, the exemplary method 160 can be carried out to facilitate visualization of any anatomic structure of a patient such as, for example, the brain, the lungs, the sinuses, and/or other hollow anatomic structures of the patient through which a medical device, such as a catheter or other similar device, may be passed. More specifically, the exemplary method 160 can facilitate visualization of the position of a medical device within the anatomic structure from multiple perspectives, including a perspective outside of an anatomic structure. Such visualization can provide unique advantages, for example, in maneuvering a medical device during any of various different medical procedures guided by, or otherwise performed in conjunction with, a three-dimensional model (e.g., a three-dimensional model representing a blood-tissue boundary in a heart cavity). The medical device, it should be appreciated, can be any medical device that is typically inserted into an anatomic structure for the purpose of diagnosis, treatment, or both and, thus, can include the catheter 104 described above with respect to FIG. 2.

The exemplary method 160 can include receiving 162 a signal indicative of location of a medical device in an anatomic structure of a patient, constructing 164 a three-dimensional model, clipping 166 the three-dimensional model to form a clipped model, and displaying 168, on a graphical user interface, a first image including the three-dimensional model and a second image including the clipped model. Clipping the three-dimensional model can include removing a first portion of the three-dimensional model relative to a first clipping surface intersecting the three-dimensional model to form the clipped model. As described in greater detail below, one or both of constructing 164 the three-dimensional model and clipping 166 the portion of the three-dimensional model to be displayed in the second image can be based on the received 162 signal indicative of the location of the medical device in the anatomic structure of the patient such that, for example, the first image and the second image displayed on the graphical user interface can provide updated (e.g., substantially real-time) spatial context to the physician as the medical device is moved in the anatomic structure. As used herein, the three-dimensional model shall be understood to include a three-dimensional representation of the anatomic structure and, optionally, a representation of the medical device relative to the anatomic structure of the patient.

In general, the first image plane and the second image plane associated with the exemplary method 160 can be any one or more of the image planes described herein (e.g., the first image plane 142 and the second image plane 148 shown in FIG. 5) and can have any manner or form of orientations relative to one another as described herein to produce corresponding changes to the respective first image and second image. Thus, for example, the second image plane can intersect the first image plane such that the corresponding first image and the corresponding second image represent different perspectives of the three-dimensional model to provide spatial context useful for maneuvering the medical device in multiple directions within the anatomic structure.

Receiving 162 the signal indicative of the location of the medical device in the anatomic structure can include receiving a signal indicative of the location of the medical device according to any one or more of the methods described herein. For example, the location of the medical device can be the location of a tip section of a catheter (e.g., the tip section 124 of the catheter 104 of FIG. 2). It should be understood, however, that the location of the medical device can also or instead include the location of any predetermined portion of the medical device in the anatomic structure.

Receiving 162 the signal indicative of the location of the medical device in the anatomic structure can include receiving the signal over a period of time. In particular, the signal indicative of the location of the medical device can be a time-varying signal. For example, the received 162 signal can be time-varying and processed such that the first image, the second image, or both can be generated or updated based on the processed received 162 signal. In general, any one or more of various, different functions can be applied to the time-series of the received 162 signal indicative of the location of the medical device to avoid, or at least lessen, the impact of abrupt motion that may be associated with changes in location of the medical device. For example, one or both of the first image and the second image can be based on low-pass filtering the received 162 signal indicative of the location of the medical device. Additionally, or alternatively, functions applied to the time-series of the received 162 signal indicative of the location of the medical device can include one or more of infinite impulse response (IIR) filters, finite impulse response (FIR) filters, non-linear filters (e.g., a median filter), and combinations thereof. More generally still, while the received 162 signal indicative of the location of the medical device is described as being filtered to control updates of the first image, the second image, or both, it should be appreciated that any other aspect of forming the first image and the second image, as the case may be, may be additionally, or alternatively, filtered to achieve smooth transitions of the respective first image and the second image. For example, the position of an image plane (e.g., one or both of the image planes 142 and 148 in FIG. 5) and/or the size of a viewing window (e.g., one or both of the viewing windows 140 and 146 in FIG. 5) can be filtered such that the respective first image and second image displayed on the graphical user interface can be depicted as moving smoothly, even when the underlying movement of the catheter is characterized by a number of rapid, small movements and/or large, abrupt transitions.

Processing the time-varying signal can be useful, for example, for improved perception of the first image, the second image, or both on the graphical user interface. For example, processing the time-varying signal of the received location of the medical device can smooth out changes in the first image and/or the second image corresponding to changes in location of the medical device such that the resulting display of the first image and the second image on the graphical user interface can be more stable (e.g., less shaky), as compared to images displayed on the graphical user interface based on an unprocessed, time-varying signal. Accordingly, processing the time-varying signal can be useful for creating changes to one or more of the first image and the second image at a rate that is both rapid enough to keep pace with changes in position of the medical device but slow enough to avoid large changes and/or many small, rapid changes to the first image and/or the second image that are more likely to interfere with the physician's use of the three-dimensional model to position the medical device.

In implementations in which the second image plane is fixed relative to the first image plane, it should be appreciated that the second image can be stabilized by, for example, processing the received 162 signal indicative of location of the medical device and, additionally or alternatively, by processing the first image itself. More generally, processing associated with the first image can stabilize the second image.

In some implementations, the received 162 signal can be processed differently with respect to the first image and the second image. For example, processing associated with the first image can result in the first image being relatively responsive to changes in the received 162 signal indicative of the location of the medical device while processing associated with the second image can result in the second image being, relative to the first image, less responsive to such changes in the received 162 signal. Alternatively, the processing associated with the respective images can be such that the second image is relatively more responsive to changes in the received 162 signal while the first image is relatively less responsive to the received 162 signal.

In general, the first image and the second image on the graphical user interface can be updated based on a change in the received 162 location signal corresponding to the location of the medical device. The update can occur at each time step or, in implementations in which the received signal is processed, the update can occur based on a combination of time steps. In each update of the first image and the second image, one or more of the steps of the exemplary method 160 can be repeated. Additionally, or alternatively, updating the first image and the second image can be based on a user input.

Constructing 164 the three-dimensional model can include updating the representation of the medical device based on the received 162 signal indicative of the location of the medical device. Thus, for example, as the medical device can be moved in the anatomic structure, such movement of the medical device can be translated into movement of the representation of the medical device relative to the three-dimensional representation of the anatomic structure. The movement of the representation of the medical device relative to the three-dimensional representation of the anatomic structure can be represented on the graphical user interface as updates are made to one or both of the first image and the second image. Accordingly, the movement of the representation of the medical device shown in the first image and the second image on the graphical user interface can serve as an analog for the physical movement of the medical device in the anatomic structure.

Constructing 164 the three-dimensional model can be based on the received 162 signal as processed according to any one or more of the methods described herein. Accordingly, as an example, constructing 164 all or a portion of the three-dimensional model can be based on low-pass filtering the received 162 signal. In certain instances, constructing 164 the three-dimensional model based on the received 162 signal as processed according to any one or more of the methods described herein can be useful for representing smooth movements of the representation of the medical device through successive updates of the first image and the second image shown on the graphical user interface.

In certain implementations, constructing 164 the three-dimensional model can include receiving one or more images (e.g., computed tomography (CT) images, magnetic resonance imaging (MRI) images, and/or boundary surfaces derived therefrom) of the anatomic structure and registering the images to a coordinate system of a sensor providing a signal indicative of location of the medical device (e.g., the magnetic position sensor 130 of FIG. 2). Thus, in such implementations, the three-dimensional representation of the anatomic structure can be based on the one or more images and constructing 164 the three-dimensional model can include rendering the representation of the medical device superimposed on the one or more images. The one or more received images can be acquired, for example, prior to the procedure. It should be appreciated, however, that these images can be acquired in real-time (e.g., using rotational angiography). Additionally, or alternatively, the three-dimensional representation can include one or more boundary surfaces generated according to any one or more of the methods described herein.

In some implementations, constructing 164 the three-dimensional model can include adding visual indicia (e.g., a tag) to the three-dimensional representation of the anatomic structure and, or instead, to another portion of the three-dimensional model. In certain implementations, the exemplary method 160 can include receiving a signal indicative of a location of a treatment applied by the medical device to the anatomic structure. In such implementations, constructing 164 the three-dimensional model can include adding visual indicia to the three-dimensional model of the anatomic structure in a location corresponding to the location of the treatment in the anatomic structure. The visual indicia can be shown on the projection of the three-dimensional representation of the anatomic structure shown in one or both of the first image and the second image. Thus, the position of the visual indicia on the three-dimensional representation of the anatomic structure can be observed from multiple perspectives. Such multiple perspectives can, it should be appreciated, facilitate application of one or more subsequent treatments relative to the visual indicia. For example, the multiple perspectives observable in the first image and the second image can facilitate application of an ablation pattern (e.g., a pattern of overlapping lesions), such as during a procedure to treat cardiac arrhythmia.

Constructing 164 the three-dimensional model can, additionally or alternatively, include adding visual indicia manually to the three-dimensional representation. For example, a physician or technician can add visual indicia corresponding to the location of an anatomic feature to the three-dimensional model (e.g., to the three-dimensional representation of the anatomic structure). For example, the exemplary method 160 can further include receiving a signal indicative of location to be tagged such that the constructed 164 three-dimensional model can include the visual indicia added to the three-dimensional model in a location on the three-dimensional model corresponding to the location being tagged. Additionally, or alternatively, the visual indicia can be added to the three-dimensional representation of the anatomic structure in one or both of the first image and the second image. Thus, for example, the physician or technician can add visual indicia to the three-dimensional representation in the second image if the view presented in the second image is more convenient for tagging than the view presented in the first image.

The visual indicia corresponding to the anatomic feature can be displayed in the respective projections of the three-dimensional model forming the first image and the second image. Thus, for example, the first image and the second image displayed on the graphical user interface can provide the physician with multiple perspectives of the medical device relative to the anatomic feature represented by the visual indicia. Such multiple perspectives can be useful, in certain instances, when moving the medical device toward or away from the anatomic feature.

In general, clipping 166 the three-dimensional model to form a clipped model to be displayed can address, among other things, a challenge associated with certain medical procedures (e.g., cardiac procedures) in which it is desirable to make observations from a perspective looking into a surface within which a medical device is contained. To address this challenge, clipping 166 the three-dimensional model can include identifying a portion (e.g., a continuous portion) of the three-dimensional model to remove. Removal, in this context, should be understood to include deleting, deemphasizing (e.g., making translucent), or otherwise modifying in the second image to differentiate the second image from the first image. Such differentiation may be advantageous when, for example, a portion of a received or acquired image is displayed in the second image. Continuing with this example, removing a portion of a received or acquired image in the second image may facilitate visualization of volumetric information such as tissue thickness or ischemia, which may otherwise be difficult to visualize on a boundary surface. Additionally, or alternatively, differentiation of the second image from the first image can improve the physician's ability to observe the position of the representation of the medical device relative to the three-dimensional model of anatomic structure. With this improved ability to make observations based on the three-dimensional model, it should be appreciated that the physician's knowledge of the position of the medical device relative to the anatomic structure during a medical procedure can be accordingly improved. For example, when the physician wishes to verify or modify the position of the medical device relative to the anatomic structure in a direction perpendicular to the first image plane, the differentiation of the second image can provide a clearer visual indication of this relative position than may be available in the first image.

The three-dimensional representation of the anatomic structure can include a boundary surface which can represent a contour of the anatomic structure being modeled. As an example, the boundary surface can represent the blood-tissue boundary such as the one depicted in the three-dimensional representation 134 of the anatomic cavity 132 described above with respect to FIGS. 3-5. Generally, clipping 166 the portion of the three-dimensional model to be displayed in the second image can include selecting less than the entirety of the boundary surface for representation in the second image. That is, the first image can include a portion of the boundary surface that is not shown in the second image.

Clipping 166 the three-dimensional model can include selecting one or more of a received or acquired image and a boundary surface generated according to any one or more of the methods described herein. More specifically, clipping 166 the three-dimensional model can include removing a first portion of the three-dimensional model relative to a first clipping surface such that the portion of the three-dimensional model that is not removed forms a clipped model.

The position of one or more of the second image plane and the first clipping surface can be based on the received 162 signal indicative of the location of the medical device.

In implementations in which the second image plane and the first clipping surface are fixed relative to one another, intersection of the first clipping surface with the three-dimensional model can be orthogonal to the first image plane. In such instances, the second image can include a projection of a portion of the boundary surface of the three-dimensional model extending in a direction away from and orthogonal to the second image plane. This arrangement of the second image plane relative to the first image plane can advantageously provide views of the three-dimensional model and the corresponding clipped model in a single coordinate system. Taking the first image 144 and the second image 150 shown in FIGS. 4 and 5 as an example, the physician can observe an outer portion of the three-dimensional representation of the anatomic structure in the first image including the three-dimensional model while observing, from a readily understood second perspective, the position of the medical device relative to an inner portion of the three-dimensional representation of the anatomic structure in the second image including the clipped model.

In some implementations, the first clipping surface can extend through the representation of the medical device. Such a first clipping surface extending through the representation of the medical device can ensure that the position of the medical device is clearly observable in the second image. That is, because the first clipping surface extends through the representation of the medical device, the position of the medical device in the second image can be generally unobscured by portions of the three-dimensional model corresponding to the three-dimensional representation of the anatomic structure. In certain implementations in which the first clipping surface extends through the representation of the medical device, the medical device can be rendered in any of various different forms. For example, the medical device can be rendered in the second image as clipped. Additionally, or alternatively, the medical device can be rendered in the second image as unclipped.

Further, or instead, the first clipping surface can be (e.g., when the first clipping surface is fixed relative to the second image plane) based on the received 162 signal indicative of the location of the medical device. Accordingly, the first clipping surface can be selected based the received 162 location signal that has been processed according to any one or more of the methods described herein, resulting in any one or more of the stabilization advantages described herein with respect to processing the received 162 location signal. Additionally, or alternatively, the position of the first clipping surface relative to the three-dimensional model can change based on changes in the location of the medical device. For example, the first clipping surface can move in accordance with movement of the medical device.

Displaying 168 the first image and the second image can include displaying images on any of various different graphical user interfaces described herein. In general, displaying 168 the first image and the second image can include displaying different parts of the three-dimensional model in the first image and the second image. If a portion of the three-dimensional model is displayed in the first image, it should be understood that the clipped model includes a subset of a portion of the three-dimensional model displayed in the first image. While a subset of the three-dimensional model is displayed in the second image, it should be appreciated that the second image can include other information useful for guiding a medical procedure. For example, the second image can, optionally, include a display of a received or acquired image that is not shown in the first image. Together, a boundary surface of the clipped model and the received or acquired image can be useful, for example, for providing a physician with feedback regarding the position of the medical device and local conditions of the anatomic structure in the vicinity of the medical device.

Figure 4:
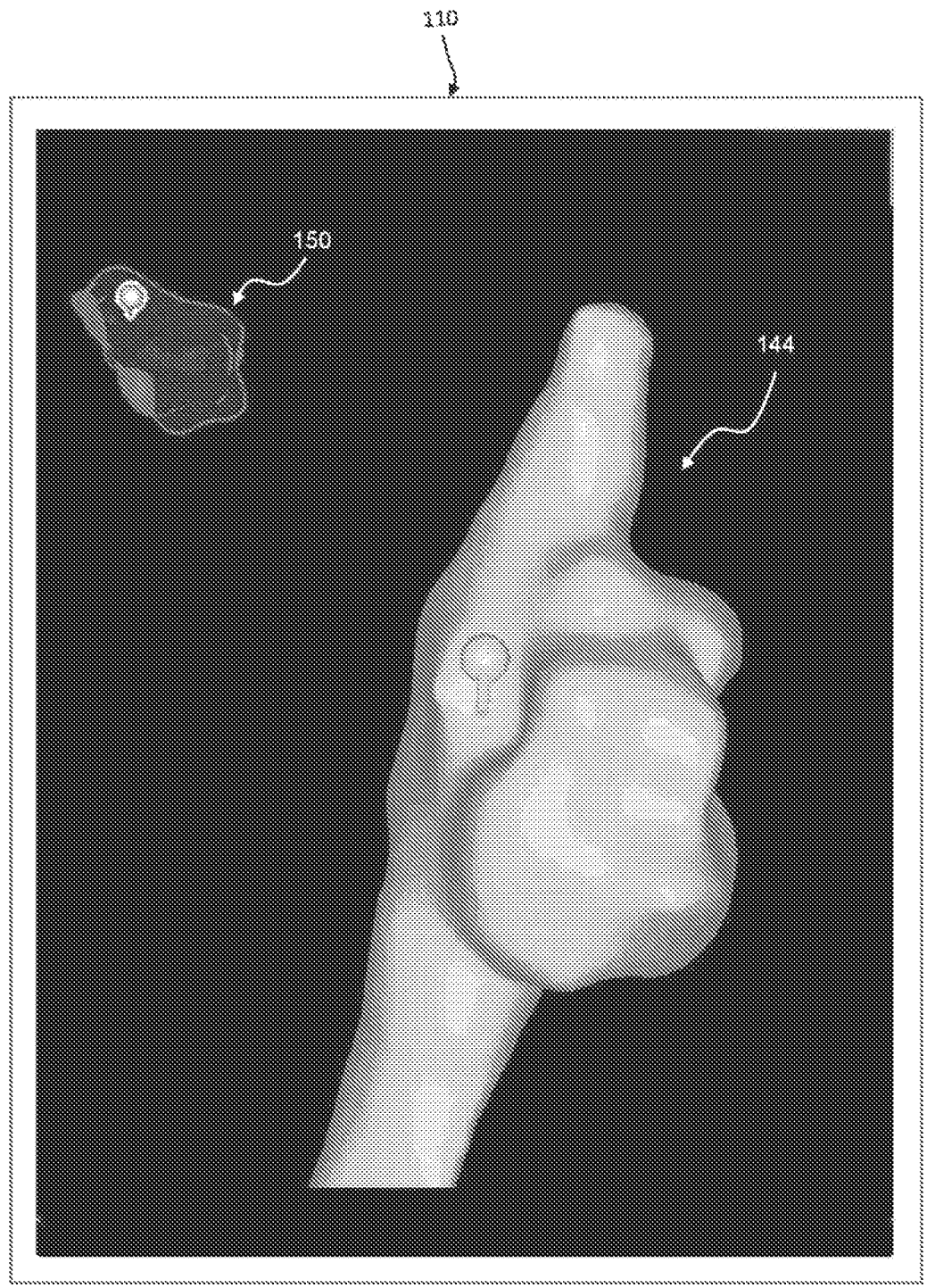
FIG. 4 is a schematic representation of a graphical user interface of the system of FIG. 1, the graphical user interface displaying projections of a three-dimensional model associated with the medical procedure of FIG. 1, and the respective projections shown in a first viewing window and a second viewing window of the graphical user interface.

The first image and the second image can be displayed 168 on a two-dimensional display such as the graphical user interface 110 described herein with respect to FIGS. 1, 4, and 5. Further, the first image can be the projection of the three-dimensional model on the first viewing window of the first image plane according to any one or more of the methods described herein. Similarly, the second image can be the projection of the clipped model on the second viewing window of the second image plane according to any one or more of the methods described herein.

In some implementations, displaying 168 the first image and the second image on the graphical user interface can include displaying the first image and the second image simultaneously on the graphical user interface. With such a simultaneous display, the physician can advantageously compare the first image to the second image to facilitate multi-directional movement of the medical device in the anatomic structure. Additionally, or alternatively, the simultaneous display of the first image and the second image can reduce the need for a physician, or a technician assisting the physician, to manipulate the graphical user interface to switch between views.

Displaying 168 the first image and the second image can include displaying the first image and the second image as different sizes on the graphical user interface. For example, given that the first image includes a projection of the three-dimensional model and the second image includes a projection of only the clipped model, the first image can be displayed as larger than the second image. Such sizing of the first image relative to the second image can be useful for displaying anatomic features in a sufficient size and with sufficient detail to be useful to the physician while allowing the physician to use the second image as an auxiliary view useful for navigating the medical device in the anatomic structure.

Displaying 168 the first image and the second image can include adjusting a zoom magnification in the respective image. For example, displaying 168 the first image and the second image can include adjusting a distance from at least one of the first image plane or the second image plane to the three-dimensional model. Also, or alternatively, displaying 168 the first image and the second image can include sizing at least one of the first viewing window or the second viewing window to change afield of view depicted in the respective image. Further, or instead, displaying 168 the first image and the second image can include moving a center of projection relative to a respective viewing window.

In certain implementations, sizing the first viewing window and, thus, the first image can be based on at least one dimension of the three-dimensional model in the first image plane. For example, the size of the first viewing window can be a multiple of a largest dimension of the three-dimensional model in the first image plane such that the entire three-dimensional model is projected onto the first viewing window to form the first image. In such implementations, it should be appreciated that the size of the first image can vary as the three-dimensional model is moved (e.g., rotated) relative to the first image plane. Additionally, or alternatively, the size of the first viewing window can be based on a user input such that, in response to the user input, the size of the three-dimensional model when projected onto the first viewing window to form the first image is varied.

In some implementations, sizing the second viewing window can be based on a bounding volume defined around the three-dimensional model. The bounding volume can be a sphere, a box, or any predetermined geometric volume. The size of the second viewing window can be based on a dimension of the bounding volume. For example, the size of the second viewing window can be based on a maximum dimension of the bounding volume. In instances in which the bounding volume is a sphere, the size of the second viewing window can be based on a diameter (e.g., a fixed multiple of the diameter) of the sphere bounding the three-dimensional model. In general, basing the size of the second viewing window on the maximum dimension of the bounding volume can facilitate maintaining a fixed size of the second image as the three-dimensional model is rotated.

The second image can include visual indicia highlighting a boundary between the representation of the medical device and the three-dimensional representation of the anatomic structure. Such a boundary, it should be understood, can be useful for providing a physician with a visual delineation between the representation of the medical device and the three-dimensional representation of the anatomic structure when the medical device is in close proximity to the surface of the anatomic structure. Such visual delineation can be particularly useful in instances in which the second image is smaller than the first image, thus making details of the second image more difficult to perceive than similar details represented in the first image. Additionally, or alternatively, such visual indicia can provide a clear indication of the spacing and relative orientation of the medical device, which can be useful, for example, for facilitating fine movement of the medical device relative to the surface of the anatomic structure (e.g., for positioning the medical device into contact with the anatomic structure).

In certain implementations, the second image can include visual indicia highlighting a contour of the boundary surface within a predetermined distance of the first clipping surface (e.g., at the intersection of the boundary surface and the first clipping surface). Such a highlighted contour can be a useful visualization guide for the physician. For example, a highlighted contour of this type can be useful for providing the physician with an indication of the shape of the anatomic structure along the first clipping surface.

In some implementations, the second image can include visual indicia highlighting an outer region of the medical device and the surface of the anatomic structure. In such implementations, as the visual indicia highlighting the boundary of the medical device moves near the surface of the anatomic structure in accordance with corresponding movement of the medical device, the boundary between these two surfaces can be readily perceivable in the second image. It should be appreciated that certain combinations of visual indicia can advantageously differentiate the outer surface of the medical device from the surface of the anatomic structure. As an example, the visual indicia delineating contours of the medical device can include thick lines rendered in a color contrasting a color palette used to represent the surface of the anatomic structure in the second image. Additionally, or alternatively, the visual indicia highlighting the boundary of the medical device can vary in color across time and/or around the boundary of the medical device to indicate a value that varies with time and/or location on the medical device, respectively. Such indicated values can be derived, for example, from measurements collected with the medical device during a procedure such as, for example: contact force; impedance; biological electrical activity; and/or acoustic or optical imaging data.

Clipping 166 the three-dimensional model can, in some instances, further include removing a second portion of the three-dimensional model relative to a second clipping surface. In such instances, the clipped model can be substantially between the first clipping surface and the second clipping surface. That is, the clipped model can be in the form of a slice, useful for visualizing complex anatomic geometry. As used herein, "substantially between" includes variations of about ±1 mm with respect to each of the first clipping surface and the second clipping surface.

Figure 8:
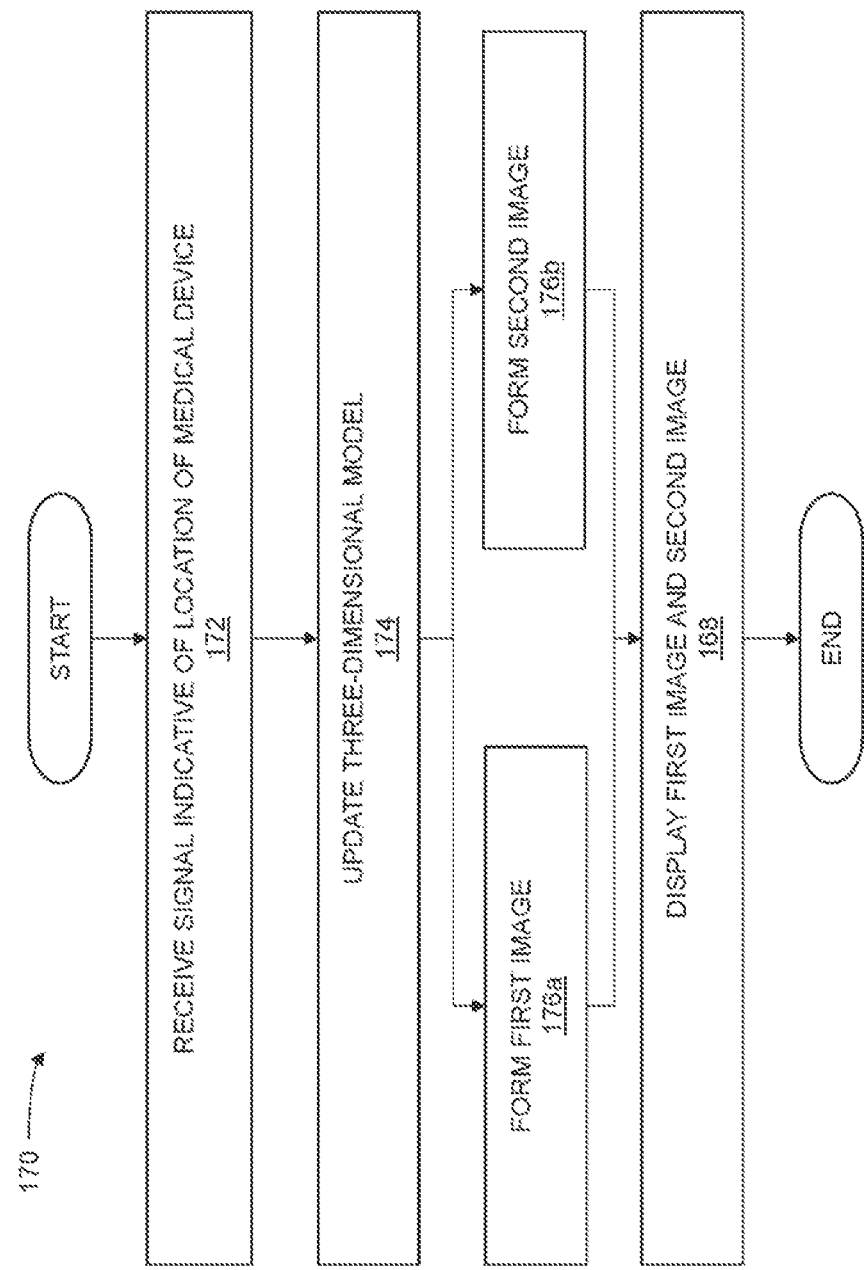
FIG. 8 is a flow chart of another exemplary method of displaying multiple images of a three-dimensional model on a graphical user interface.

FIG. 8 is a flowchart of another exemplary method 170 of displaying multiple images of a three-dimensional model on a graphical user interface. In general, unless otherwise specified or made clear from the context, the exemplary method 170 can facilitate visualization of a medical device in an anatomic structure in a manner analogous to the facilitated visualization achieved by the exemplary method 160. Further, like the exemplary method 160 (FIG. 7), the exemplary method 170 can be implemented using the system 100 (FIG. 1) and any one or more components thereof. Further still, to the extent the exemplary method 170 differs from the exemplary method 160 (FIG. 7), it will be understood that any one or more steps of the exemplary method 170 may be combined with or replace any one or more steps of the exemplary method 160 to display multiple images of a three-dimensional model on a graphical user interface.

The exemplary method 170 can include receiving 172 a signal indicative of a location of a medical device in an anatomic structure of a patient, updating 174 a three-dimensional model, forming 176a a first image including a projection of the updated three-dimensional model, forming 176b a second image including a projection of the updated three-dimensional model, and displaying 178 the first image and the second image on a graphical user interface.

Receiving 172 the signal indicative of the location of the medical device in the anatomic structure can include any of the various different methods of receiving a location signal described herein. Such an exemplary method of receiving 172 the signal indicative of location can include, therefore, a signal received from a magnetic position sensor such as the magnetic position sensor 130 described with respect to FIG. 2.

The three-dimensional model can be updated 174 based on the received 172 signal indicative of the location of the medical device in the anatomic structure and can include a three-dimensional representation of the anatomic structure and a representation of the medical device relative to the anatomic structure. The three-dimensional model can be any of the various different three-dimensional models described herein such that, for example, the three-dimensional model is inclusive of the three-dimensional model 136 described with respect to FIGS. 4-6. Accordingly, the three-dimensional representation of the anatomic structure can be based on one or more received images (e.g., computed tomography (CT) images and/or magnetic resonance imaging (MRI) images) of the anatomic structure, with the images registered to a coordinate system of a sensor providing a signal indicative of location of the medical device (e.g., the magnetic position sensor 130 of FIG. 2). Thus, in such instances, updating 174 the three-dimensional model can include updating the representation of the medical device superimposed on the one or more images. The one or more received images can be acquired, for example, prior to the procedure. It should be appreciated, however, that these images can be acquired in real-time (e.g., using rotational angiography).

Updating 174 the three-dimensional model can be based on the received 172 signal indicative of the location of the medical device in the anatomic structure. Accordingly, in certain implementations, updating 174 the three-dimensional model can include processing the received 172 signal according to one or more of the methods of processing described herein such as, for example, low-pass filtering. That is, the updated 174 three-dimensional model can be based on the received 172 signal that has been processed. Additionally, or alternatively, processing can be applied to one or more steps of the exemplary method 170 to achieve corresponding stabilization of the first image, the second image, or both on the graphical user interface.

Forming 176a the first image and forming 176b the second image can include projecting the three-dimensional model according any one or more of the methods described herein and, in particular, such methods described with respect to FIG. 5. The first image can include a projection, on a first viewing window of a first image plane, of at least one portion of the updated three-dimensional model. The second image can include another portion of the updated three-dimensional model. In certain implementations, the portion of the three-dimensional model projected on the second image plane can be less than the at least one portion of the updated three-dimensional model projected on the first viewing window such that, for example, an inner portion of the three-dimensional model can be more readily observable in the second image than in the first image.

The first image plane and the second image plane can be any one or more of the image planes described herein such that, as one example, the first image plane and the second image plane can intersect one another to produce complementary views of the three-dimensional model in the first image and the second image. Further, the first image plane can be adjusted according to any of the various different methods described herein. Such adjustment of the first image plane, it should be appreciated, can produce a corresponding change in the second image plane. For example, the first image plane can be adjusted while the second image plane is maintained in a fixed orientation (e.g., a fixed orthogonal relationship) relative to the first image plane, and the corresponding second image can change in a fixed relationship to the first image as the first image plane changes.

The first image plane can be orientated relative to the received 172 location of the medical device. In such instances, the first image can provide a view of the three-dimensional model from a perspective of the medical device as the medical device is moved relative to the anatomic structure. Such a perspective can be useful, for example, for fine three-dimensional manipulation of the medical device relative to the anatomic structure (e.g., such as to establish contact between the medical device and the anatomic structure during an ablation treatment). In certain implementations, orienting the first image plane relative to the received 172 location of the medical device can include orienting the first image plane in a direction perpendicular to an average of surface normal vectors along a portion, closest to the medical device, of a boundary surface of the anatomic structure in the three-dimensional model. That is, more generally, orienting the first image plane relative to the received 172 location of the medical device can include moving the first image plane based on one or more local features of the anatomic structure in the vicinity of the medical device, facilitating, for example, three-dimensional manipulation of the medical device relative to a surface of the anatomic structure.

Displaying 178 the first image and the second image on the graphical user interface can be carried out according to any one or more of the methods described herein. Thus, for example, displaying 178 the first image and the second image can include displaying the first image and the second image simultaneously on the graphical user interface. Additionally, or alternatively, the graphical user interface can be any one or more of the graphical user interfaces described herein including, for example, the graphical user interface 110 described with respect to FIGS. 1 and 5.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals.

It will further be appreciated that a realization of the processes or devices described above may include computer-executable code created using a structured programming language such as C, an object oriented programming language such as C++, or any other high-level or low level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices.

In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. A method comprising:
   receiving, from at least one position sensor, a location signal indicative of a location of a medical device in an anatomic structure of a patient;
   based at least in part on the received location signal, constructing a three-dimensional model including a three-dimensional representation of the anatomic structure and a representation of the medical device relative to the anatomic structure;
   based at least in part on the received location signal, clipping the three-dimensional model, clipping the three-dimensional model including removing a portion of the three-dimensional model relative to a clipping surface extending through the three-dimensional model to form a clipped model, wherein a location of the clipping surface through the three-dimensional model is based on the received location signal; and
   displaying, on a graphical user interface, a first image and a second image, wherein the first image includes a projection of the three-dimensional model on a first viewing window of a first image plane, and the second image includes a projection of the clipped model on a second viewing window of a second image plane.

2. The method of claim 1, wherein constructing the three-dimensional model includes receiving one or more images of the anatomic structure and registering the images to a coordinate system of a sensor providing the location signal indicative of the location of the medical device.

3. The method of claim 1, wherein constructing the three-dimensional model includes updating the representation of the medical device based on the received location signal.

4. The method of claim 1, wherein the received location signal is a time-varying location signal and clipping the three-dimensional model further comprises:
   processing the time-varying location signal and selecting the clipping surface based on the processed, time-varying location signal.

5. The method of claim 4, wherein processing the time-varying location signal includes low pass filtering the time-varying location signal.

6. The method of claim 1, further comprising adjusting the first image plane and maintaining the second image plane in a fixed orientation relative to the first image plane.

7. The method of claim 6, wherein the second image plane is restricted to a direction superior to the representation of the location of the medical device in the three-dimensional model.

8. The method of claim 6, wherein adjusting the first image plane includes orienting the first image plane relative to the location of the medical device in the anatomic structure of the patient.

9. The method of claim 1, wherein displaying the first image and the second image on the graphical user interface includes adjusting the size of the three-dimensional model as projected onto one or both of the first viewing window and the second viewing window.

10. A system comprising:
    a memory;
    a processing unit configured to:
        receive, from at least one position sensor, a location signal indicative of a location of a medical device in an anatomic structure of a patient;
        based at least in part on the received location signal, construct a three-dimensional model including a three-dimensional representation of the anatomic structure and a representation of the medical device relative to the anatomic structure; and
        based at least in part on the received location signal, clip the three-dimensional model, clipping the three-dimensional model including removing a portion of the three-dimensional model relative to a clipping surface extending through the three-dimensional model to form a clipped model, wherein a location of the clipping surface through the three-dimensional model is based on the received location signal; and
    a graphical user interface (GUI) configured to display a first image and a second image, wherein the first image includes a projection of the three-dimensional model on a first viewing window of a first image plane, and the second image includes a projection of the clipped model on a second viewing window of a second image plane.

11. The system of claim 10, wherein constructing the three-dimensional model includes receiving one or more images of the anatomic structure and registering the images to a coordinate system of a sensor providing the location signal indicative of the location of the medical device.

12. The system of claim 10, wherein constructing the three-dimensional model includes updating the representation of the medical device based on the received location signal.

13. The system of claim 10, wherein the received location signal is a time-varying signal and clipping the three-dimensional model further includes processing the time-varying signal and selecting the clipping surface based on the processed, time-varying signal.

14. The system of claim 13, wherein processing the time-varying signal includes low pass filtering the time-varying signal.

15. The system of claim 10, further comprising adjusting the first image plane and maintaining the second image plane in a fixed orientation relative to the first image plane.

16. The system of claim 15, wherein the second image plane is restricted to a direction superior to the representation of the location of the medical device in the three-dimensional model.

17. The system of claim 15, wherein adjusting the first image plane includes orienting the first image plane relative to the location, in the anatomic structure of the patient, of the medical device.

18. The system of claim 10, wherein displaying the first image and the second image includes adjusting the size of the three-dimensional model as projected onto one or both of the first viewing window and the second viewing window.

* * * * *